US 9,314,315 B2

(12) United States Patent
Wong

(10) Patent No.: US 9,314,315 B2
(45) Date of Patent: Apr. 19, 2016

(54) DEVICE FOR HOLDING SMALL DENTAL PARTS

(71) Applicant: Wong Technology LLC, Federal Heights, CO (US)

(72) Inventor: Alan Wong, Westminster, CO (US)

(73) Assignee: Wong Technology LLC, Federal Heights, CO (US)

( * ) Notice: Subject to any disclaimer, the term of this patent is extended or adjusted under 35 U.S.C. 154(b) by 72 days.

(21) Appl. No.: 14/151,976

(22) Filed: Jan. 10, 2014

(65) Prior Publication Data

US 2015/0196370 A1     Jul. 16, 2015

(51) Int. Cl.
| | |
|---|---|
| *A61C 3/04* | (2006.01) |
| *A61C 19/02* | (2006.01) |
| *B25H 3/06* | (2006.01) |
| *A61C 1/14* | (2006.01) |
| *A61B 19/02* | (2006.01) |
| *A61C 19/00* | (2006.01) |

(52) U.S. Cl.
CPC .............. *A61C 3/04* (2013.01); *A61B 19/0256* (2013.01); *A61B 2019/0258* (2013.01); *A61C 1/14* (2013.01); *A61C 19/001* (2013.01); *A61C 19/02* (2013.01); *B25H 3/06* (2013.01); *Y10T 29/49826* (2015.01)

(58) Field of Classification Search
CPC ...... A61C 19/02; A61C 2202/00; A61C 3/04; A61C 1/14; A61C 1/145; A61B 19/0256; A61B 19/0257; A61B 19/0271; A61B 2019/0258; A61B 2019/0259; H01F 7/0252; B25H 3/06; Y10S 206/818
USPC ........ 206/63.5, 350, 368, 369, 572, 379, 370, 206/558, 564, 570, 438, 372, 576; 433/77, 433/300, 164, 49, 50; D24/176, 177, 229, D24/227; 248/309.4; 211/126.1–126.16, 211/85.13, 60.1, 70.6, DIG. 1; 335/285
See application file for complete search history.

(56) References Cited

U.S. PATENT DOCUMENTS

| | | | | |
|---|---|---|---|---|
| 935,419 | A * | 9/1909 | Smith | 206/369 |
| 979,493 | A * | 12/1910 | Holtz | 206/368 |
| 1,659,315 | A * | 2/1928 | Dailey | 206/63.5 |
| 1,704,122 | A * | 3/1929 | Cohen | 206/368 |
| 2,217,514 | A * | 10/1940 | Henry | 220/628 |
| 2,414,653 | A * | 1/1947 | Lookholder | A47K 1/09 15/220.2 |
| 2,491,771 | A * | 12/1949 | Roos | 206/369 |
| 2,657,342 | A * | 10/1953 | Stem | B03C 1/288 335/305 |
| 2,964,201 | A * | 12/1960 | Huffman | A47F 5/02 206/818 |
| 3,029,824 | A * | 4/1962 | Goodell | A24F 19/00 131/240.1 |
| 3,337,042 | A * | 8/1967 | Bergendal et al. | 206/63.5 |
| 3,366,230 | A * | 1/1968 | Loran | 206/63.5 |
| 3,419,832 | A * | 12/1968 | Baermann | B25H 3/04 206/818 |
| 3,442,376 | A * | 5/1969 | McDivit | A61C 3/04 206/63.5 |

(Continued)

*Primary Examiner* — Mickey Yu
*Assistant Examiner* — Gideon Weinerth
(74) *Attorney, Agent, or Firm* — William P. O'Meara, Esq.; Klaas, Law, O'Meara & Malkin PC

(57) ABSTRACT

A device for holding small dental parts may include a bowl member having central recess defined by a recess wall that has an inner surface adapted to engage dental parts and an outer surface. A plurality of magnets may be arranged around the recess wall and may be position adjacent to the outer surface of the recess wall. Also, a magnetic bowl system, which provides a bowl member that is disposable to avoid cross contamination and a separate magnet holder member that is reusable.

6 Claims, 4 Drawing Sheets

(56) References Cited

U.S. PATENT DOCUMENTS

| | | | | |
|---|---|---|---|---|
| 3,667,079 | A * | 6/1972 | Hagglund | A61C 19/00 108/25 |
| 3,765,564 | A * | 10/1973 | Persson | 433/25 |
| 3,776,371 | A * | 12/1973 | Linger | 206/1.7 |
| 3,868,016 | A * | 2/1975 | Szpur et al. | 206/350 |
| 4,011,944 | A * | 3/1977 | Cooley et al. | 206/557 |
| 4,184,251 | A * | 1/1980 | Kuboki | 433/29 |
| D261,934 | S * | 11/1981 | Porteous | D24/227 |
| D283,774 | S * | 5/1986 | Bratcher | D7/396.1 |
| D288,234 | S * | 2/1987 | Blatherwick | D24/230 |
| D293,820 | S * | 1/1988 | Guth | D24/230 |
| D302,467 | S * | 7/1989 | Holewinski | D24/181 |
| 4,852,738 | A * | 8/1989 | Craig et al. | 206/369 |
| 5,069,339 | A * | 12/1991 | Hsu | B43M 99/009 206/340 |
| 5,314,625 | A * | 5/1994 | Farnelli | B01D 21/0009 184/6.25 |
| D351,661 | S * | 10/1994 | Fischer | D24/176 |
| 5,405,004 | A * | 4/1995 | Vest et al. | 206/350 |
| D367,757 | S * | 3/1996 | Liu | 224/183 |
| D372,125 | S * | 7/1996 | Frazier | D3/315 |
| D402,767 | S * | 12/1998 | Davis | D24/227 |
| D403,433 | S * | 12/1998 | Linden | D24/227 |
| D405,611 | S * | 2/1999 | Hawkins | D3/313 |
| 5,941,381 | A * | 8/1999 | James | A47L 13/51 206/229 |
| 6,041,717 | A * | 3/2000 | Kubat | B60R 11/06 108/44 |
| D423,679 | S * | 4/2000 | Jenkins | D24/227 |
| 6,056,132 | A * | 5/2000 | Becker | B25H 3/04 211/164 |
| D438,634 | S * | 3/2001 | Merry | D24/227 |
| D441,090 | S * | 4/2001 | Broyles | D24/176 |
| D450,130 | S * | 11/2001 | Goldstein | D24/227 |
| D472,712 | S * | 4/2003 | Sagen | D3/313 |
| D482,451 | S * | 11/2003 | Page | D24/176 |
| 6,811,127 | B1 * | 11/2004 | Shiao | 248/206.5 |
| 7,188,629 | B2 * | 3/2007 | Mehes | A46B 17/00 132/310 |
| D618,795 | S * | 6/2010 | Nguyen | D24/139 |
| D618,821 | S * | 6/2010 | Larsen | D24/227 |
| D638,137 | S * | 5/2011 | Gross | D24/227 |
| 7,934,449 | B2 * | 5/2011 | Anderson | B65D 1/36 206/508 |
| 8,328,013 | B2 * | 12/2012 | Stevens | B44D 3/123 206/373 |
| D687,225 | S * | 8/2013 | Baker | D3/313 |
| 9,033,198 | B2 * | 5/2015 | Escherich | B25H 3/003 224/183 |
| 9,153,152 | B1 * | 10/2015 | Elmer | H01F 7/00 |
| 2003/0038100 | A1 * | 2/2003 | Liu | B25H 3/04 211/88.01 |
| 2004/0040106 | A1 * | 3/2004 | Funk | B23Q 11/0064 15/104.001 |
| 2005/0205450 | A1 * | 9/2005 | Leitch | A61B 19/0288 206/438 |
| 2005/0258059 | A1 * | 11/2005 | Joyce | B25H 3/003 206/378 |
| 2006/0042977 | A1 * | 3/2006 | Sandel | A61B 19/0271 206/370 |
| 2008/0179268 | A1 * | 7/2008 | Jang | B25H 3/06 211/126.1 |
| 2009/0218463 | A1 * | 9/2009 | Winnard | B25H 3/04 248/309.4 |
| 2009/0218741 | A1 * | 9/2009 | Winnard | B25H 3/06 269/8 |
| 2013/0105344 | A1 * | 5/2013 | Hartley | A61B 1/00062 206/363 |
| 2013/0118936 | A1 * | 5/2013 | Chang | 206/350 |
| 2013/0276675 | A1 * | 10/2013 | Guerrero | B25H 3/06 108/27 |
| 2013/0334083 | A1 * | 12/2013 | Bugnard | A61B 19/026 206/370 |
| 2014/0014544 | A1 * | 1/2014 | Bugnard | A61B 19/026 206/369 |
| 2014/0231302 | A1 * | 8/2014 | Goyal | A61B 19/026 206/571 |
| 2014/0285295 | A1 * | 9/2014 | Liimatta | H01F 7/0252 335/285 |
| 2014/0299739 | A1 * | 10/2014 | Bradow | A61B 19/0256 248/683 |
| 2014/0332538 | A1 * | 11/2014 | Chen | A47G 19/02 220/574 |

* cited by examiner

DEVICE FOR HOLDING SMALL DENTAL PARTS

BACKGROUND

Many dental procedures require a dentist to use several different dental instruments and other small dental parts. For example, the procedure of crowning a tooth typically requires a dentist to use the following small dental parts: various carbide burs, diamond burs, mandrels, and disks, rubber points of various sizes, latch burs, finishing burs and finishing disks, mini micro brushes for peridex, etch, and bonding agents. For an implant procedure the following small parts are usually required: implant screws, implant abutments, transfer copings, and implant torque wrench and latch. Keeping such dental instruments and other small parts organized and readily available to the dentist, even with the help of a dental assistant, is an ongoing challenge.

SUMMARY

A device for holding small dental parts is described. The device includes a bowl member having a central recess defined by a recess wall. The recess wall has an inner surface, which engages the small dental parts. The recess wall also has an outer surface with a plurality of magnets positioned adjacent to it and arranged around it. Magnetic force holds small dental parts made from magnetic material against the inner surface of the recess wall.

The recess wall may have a flat bottom portion and a sloped sidewall portion. The sidewall portion is divided into a number of sections. The magnets may be positioned adjacent to several of the sections of the sidewall portion. The bowl member may also have a top rim surface with spaced apart teeth thereon that are adapted to receive and hold larger ones of the small dental parts. The teeth may be positioned adjacent to sections of the sidewall portion that do not have magnets near them.

The magnets may be supported by a magnet holder member, which is separate from the bowl member. The magnet holder member may be constructed such that it is readily attachable to and detachable from the bowl member. Because a magnet holder member is attached to a surface of a bowl member that is on the side opposite to the side that receives the small dental parts, there is no risk of contaminating the support plate with the small dental parts so long as the bowl member remains attached to the magnet holder member. Thus, the magnet holder member may be reused. Since the bowl member receives the small dental parts, it must be sterilized or discarded after every use. For a typical dental practice, only a small number of the relatively expensive magnet holder members are needed as compared to the number of relatively inexpensive bowl members. The bowl members are designed with tapered walls and have a nesting configuration that allows a large number of bowl members to be stacked to conserve space.

DETAILED DESCRIPTION

As used herein, spatial reference terms such as up, down, bottom, top, vertical, horizontal, lateral, left, right, etc., are used in a relative sense for establishing a frame of reference used for describing the spatial relationship between objects or various parts of an object. They are not used in an absolute sense that implies the orientation of an object in a field of gravity. Using the term "top" in this relative sense with a table that is described as having "a top surface that supports a computer" such surface would be correctly referred to as the "top surface" of the desk even if the desk were flipped upside down or resting on its side.

Figure 1:
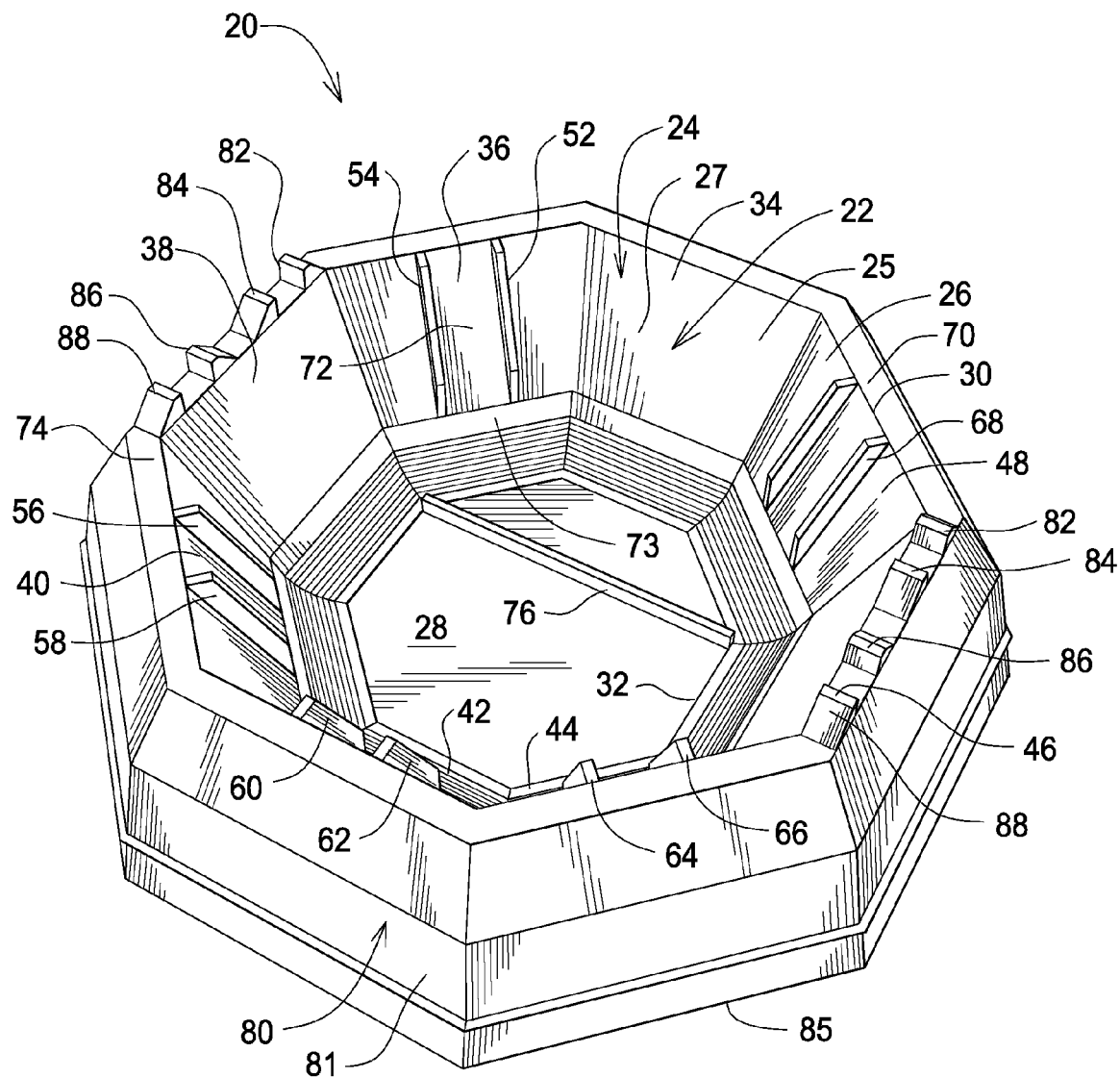
FIG. 1 is a top isometric view of a bowl member of a device for holding small dental parts.
Figure 4:
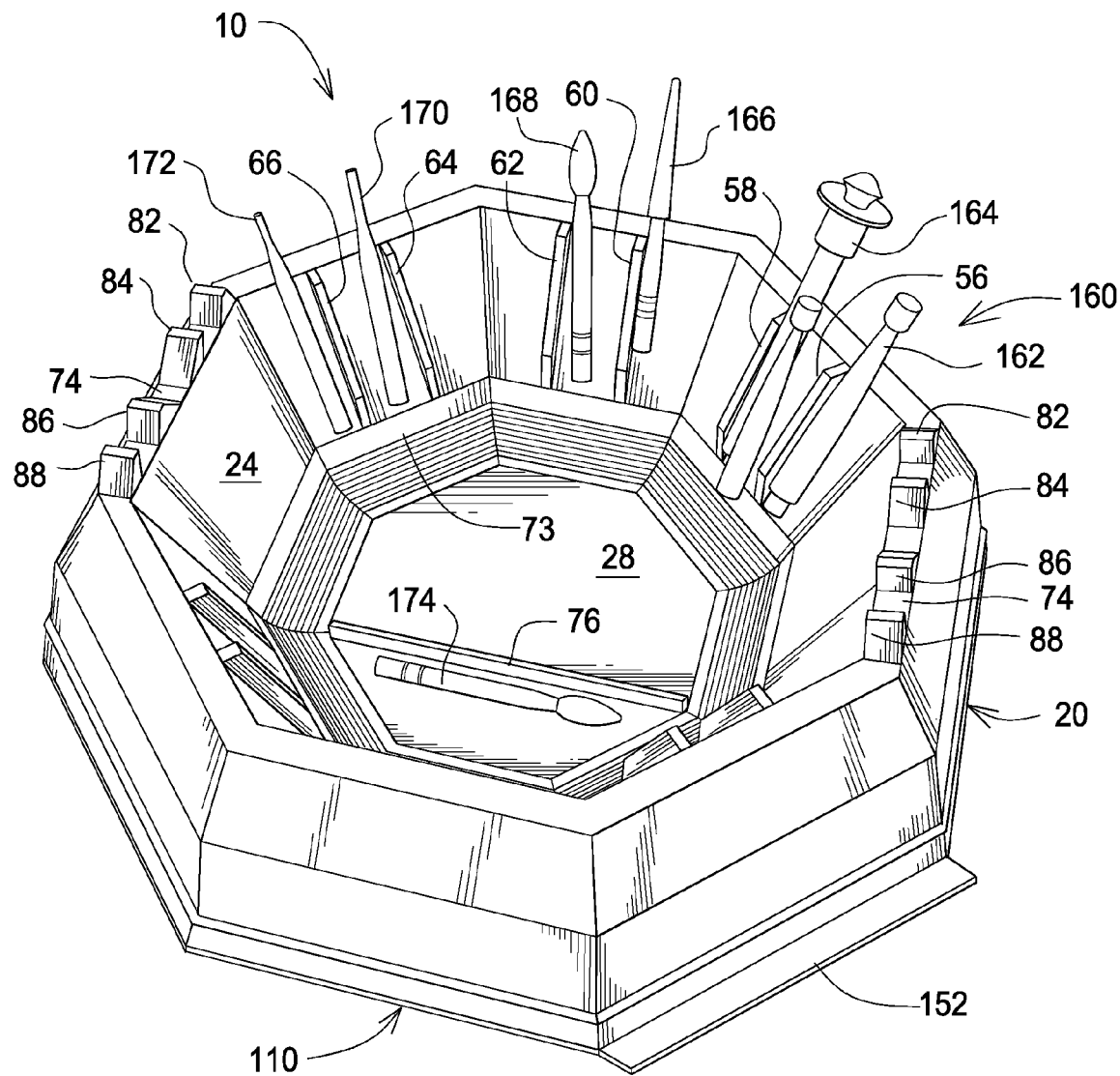
FIG. 4 as a top isometric view of the device of FIG. 1 holding a plurality of small dental parts.

FIG. 1 shows a bowl member 20 of a dental tool holder 10, FIG. 4. The bowl member 20 has a central recess 22 that is defined by a recess wall 24. The recess wall 24 has an inner surface 25 and an outer surface 27, FIG. 2. The inner surface 25 has a downwardly and inwardly sloping portion 26 and a horizontally disposed portion 28. The recess wall 24 may have a polygonal upper edge 30 and a corresponding polygonal bottom edge 32. The distance between opposite sides of the octagonal bottom edge 32 may be about 27.7 mm. The downwardly and inwardly sloping wall portion 26 may comprise eight trapezoidal wall sections 34 extending between the upper and bottom edges 30, 32. A plurality of upwardly extending rib pairs: 52, 54; 56, 58; 60, 62; 64, 66; and 68, 70, are provided on wall sections 36, 40, 42, 44, and 48, respectively. These rib pairs may be provided to separate small dental parts or tools that lie against the inner surface 25 of the downwardly and inwardly sloping portion 26. The ribs may each have a length of about 14.0 mm. A gap 72 may be provided between each pair of ribs e.g. 52, 54. The gap distance of each gap 72 may be about 5.4 mm. A lower horizontal rim 73 may extend around the inner surface 27 near the bottom of each of the ribs 52, 54, etc.

A laterally extending bottom rib 76 may be provided on the inner surface 25 of the horizontally disposed bottom portion 28 of the recess wall 24. The purposes of the rib 76 are described in detail below.

Figure 2:
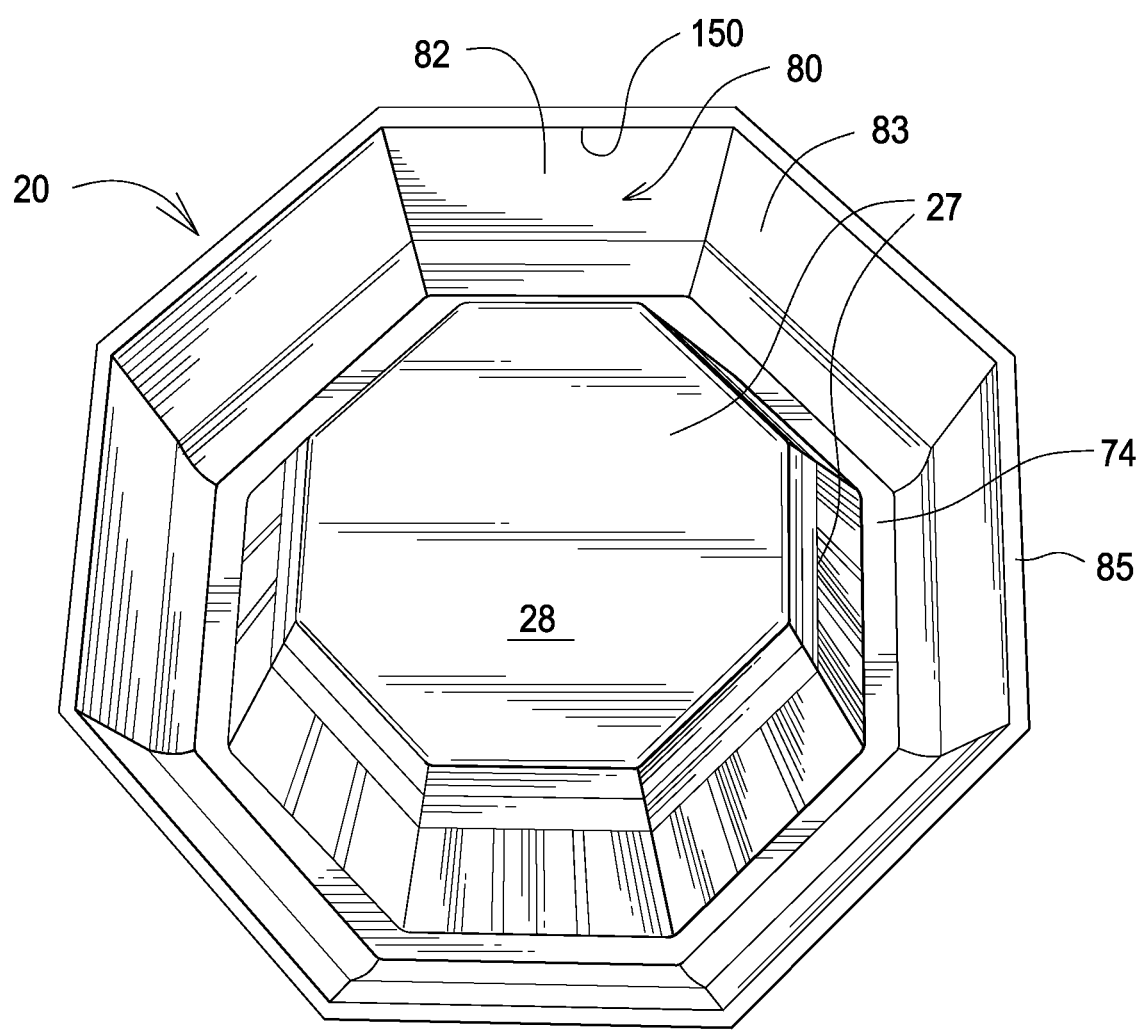
FIG. 2 is a bottom isometric view of the bowl member of FIG. 1.

An upper horizontally disposed wall 74 may be integrally formed at the top edge 30 of the recess wall 24, as shown in FIGS. 1 and 2. The upper horizontally disposed wall 74 may have an octagonal ring shaped configuration with a ring width about 2.5 mm. Wall 74 integrally connects the recess wall 24 to a generally downwardly and outwardly extending skirt shaped flange 80. The flange 80 has a first surface 81, FIG. 1, and an opposite second service 83, FIG. 2. The flange 80 terminates in an octagonal bottom edge portion 85, as best shown in FIG. 2. Edge portion 85 may lie in substantially the same plane as the outer surface 27 of the horizontally disposed portion 28 of the recess wall 24. The flange 80 substantially increases the width of the bowl member 20, increasing its stability. In one embodiment the length of each side of the octagonal bottom rim 85 may be about 27.7 mm. In one embodiment the entire bowl member 20 is constructed from a resilient plastic material such as a thermoforming grade of high impact polystyrene.

Figure 3:
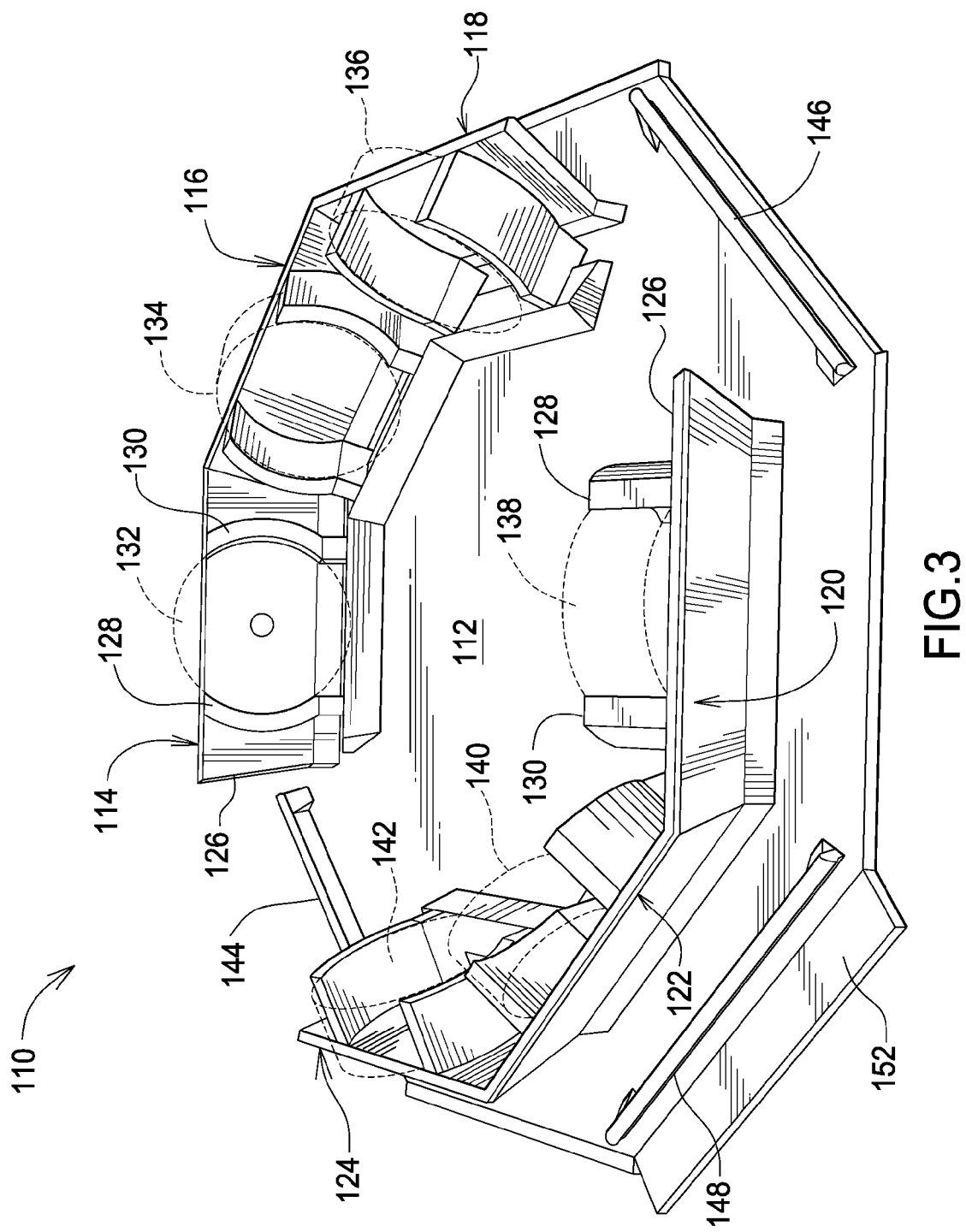
FIG. 3 is a top isometric view of a magnet support plate.

FIG. 3 illustrates a magnet holder member 110. The magnet holder member 110 includes a generally octagonal plate 112. A plurality of magnet backing plates 114, 116, 118, 120, 122, 124 are mounted on the octagonal plate 112 and are inclined upwardly and outwardly at the same angle as the sidewalls of the trapezoidal wall sections 34, 36, 38, etc., of the bowl member 20. A pair of arcuate brackets 128 and 130 are attached to each backing plate 114, 116, etc. Disc shaped magnets 132, 134, 136, 138, 140, 142, are supported by each pair of brackets 128, 130. In one embodiment each magnet has a diameter of about 10 mm and an axial length of about 4.3 mm.

Ribs 144, 146 and 148 (only three of four are visible in FIG. 3) are arranged around a peripheral portion of the octagonal plate 112. Referring to FIG. 2, an inwardly extending peripheral lip 150 extends around the second surface 83 of skirt portion 80. The ribs 144, 146, etc., FIG. 3, each have an upper edge portion that co-acts with the lip 150 to provide a snap-fit relationship. When the bowl member 20 is positioned above the octagonal magnet holder member 110 with the respective peripheries aligned, downward pressure on the bowl member 20 causes the ribs 144, 146, etc., to snap into a locking relationship with the lip 150. The bowl member 20 is thereby held in fixed relationship with the magnet holder member 110. An integrally formed foot portion 152 extends laterally outwardly from the octagonal magnet holder member 110. This foot portion 152 may be grasped to facilitate prying removal of the magnet holder member 110 from the bowl member 20.

FIG. 4 illustrates the small dental parts holding device 10 with a plurality of dental instruments 160 supported on the recess wall 24. The dental instruments may include individual instruments 162, 164, 166, 168, 170, 172 supported on the inner surface 25 of recess wall 24 between the ribs 56, 58, etc. Longer dental instruments, not shown, may be supported on the horizontal wall surface 74 between opposed upwardly projecting teeth 82, 84, 86, 88 on diametrically opposed sides of the bowl member upper horizontally disposed wall 74. (In another embodiment, the teeth project downwardly rather than upwardly. In yet another embodiment the teeth are replaced by oppositely positioned, downwardly concave surfaces portions in the horizontal wall surface 74.) A used drill bit 174 is positioned in the smaller section of the horizontally disposed portion 28 adjacent to rib 76. Material removed from a patient's mouth, such as a crown (not shown) may be positioned on the other side of rib 76. The rib 76 serves a number of purposes. One purpose is to separate burs. Some burs can be reused while others need to be discarded. The rib 76 separates the burs and organizes reusable burs. The rib 76 can also separate the central recess 22 into one side with adjacent magnets 132, 134, etc., and a second side with no adjacent magnets. The magnets 132, 134, etc., can be used to keep burs to be reused in a vertical stack for easy retrieval. The non-magnet side can be used to hold discarded burs. The rib 76 can also be used to separate implant screws from implant abutments. The purpose of the rib 76, generally, is to create more options for better organization of small dental parts.

It may be seen from FIGS. 1 and 2 that the bowl member 20 has a stackable shape that allows a plurality of identical bowl members 20 to be nested together in a compact, space saving relationship. The two part construction of the device 10 enables a dentist to buy and keep on hand only a relatively few of the reusable and relatively expensive magnet support members 110. This is because the magnet support members 110 ordinarily do not come into contact with the small dental Instruments 160 or dental artifacts from a patient's mouth. Such items are placed in the bowl members 20, which are relatively inexpensive and may thus be discarded after use by each patient.

While illustrative embodiments of a device for holding small dental parts have been described in detail herein, it is to be understood that the inventive concepts disclosed may be otherwise variously embodied and employed and that the appended claims are intended to be construed to include such variations except insofar as limited by the prior art.

What is claimed is:

1. A device for holding small dental parts comprising:
    a bowl member having a central recess defined by a recess wall with an inner surface adapted to engage dental parts and an outer surface, said recess wall comprising a generally downwardly and inwardly sloping portion and a generally horizontally disposed portion connected to said downwardly and inwardly sloping portion, said generally downwardly and inwardly sloping portion comprising polygonal upper and lower edges with a plurality of generally flat trapezoidal wall sections extending between said upper and lower edges; and a generally downwardly and outwardly extending flange connected to said outwardly extending recess wall by an outwardly extending wall with projecting teeth adapted to receive dental parts therebetween, said bowl member having a shape that facilitates nestingly stacking multiple members identical to said bowl member; and
    a plurality of magnets arranged around said recess wall in adjacent relationship with said outer surface thereof wherein said plurality of magnets are aligned with different ones of said generally flat trapezoidal wall sections and are supported by arcuate magnet holder brackets on a magnet support member that is readily engageable with and disengageable from said bowl member.

2. The device of claim 1 wherein said arcuate magnet holder brackets comprise a first bracket adapted to engage a first peripheral portion of a cylindrical magnet with a portion of said magnet extending above said first bracket and a second bracket adapted to engage a second peripheral portion of said cylindrical magnet with a portion of said magnet extending above said second bracket.

3. The device of claim 1 wherein said arcuate magnet holder brackets are mounted on a plurality of magnet backing plates.

4. The device of claim 3 wherein said magnet backing plates slope upwardly and outwardly from a horizontally disposed plate portion of said magnet support member.

5. The device of claim 3 wherein said magnet backing plates extend generally parallel to corresponding ones of said plurality of generally flat trapezoidal wall sections of said bowl member.

6. The device of claim 1 wherein said bowl member generally and outwardly extending flange comprises a peripheral lip and wherein said magnet support member comprises a plurality of ribs that co-act with said peripheral lip to selectively attach and detach said bowl member and said magnet support member.

\* \* \* \* \*